United States Patent
Krug et al.

(10) Patent No.: US 8,465,766 B2
(45) Date of Patent: Jun. 18, 2013

(54) WOUND AND MUCOUS MEMBRANE DISINFECTANT

(75) Inventors: Barbara Krug, Hamburg (DE); Sven Dabek, Hamburg (DE); Kai-Martin Mueller, Hamburg (DE); Marco Rudolf, Basel (CH); Hanns Pietsch, Hamburg (DE); Hiltraut Pietsch, legal representative, Hamburg (DE); Christiane Ostermeyer, Hamburg (DE)

(73) Assignee: Bode Chemie GmbH, Hamburg (DE)

( * ) Notice: Subject to any disclaimer, the term of this patent is extended or adjusted under 35 U.S.C. 154(b) by 0 days.

(21) Appl. No.: 13/236,847

(22) Filed: Sep. 20, 2011

(65) Prior Publication Data

US 2012/0070510 A1 Mar. 22, 2012

Related U.S. Application Data

(63) Continuation of application No. 12/064,746, filed as application No. PCT/EP2006/064836 on Jul. 31, 2006, now abandoned.

(30) Foreign Application Priority Data

Aug. 26, 2005 (DE) .......................... 10 2005 041 730
Dec. 9, 2005 (DE) .......................... 10 2005 058 978

(51) Int. Cl.
*A61K 9/66* (2006.01)
(52) U.S. Cl.
USPC ........................................ 424/455; 424/605
(58) Field of Classification Search
None
See application file for complete search history.

(56) References Cited

U.S. PATENT DOCUMENTS

| | | | |
|---|---|---|---|
| 4,542,125 A | 9/1985 | Gorman et al. | |
| 4,839,372 A | 6/1989 | Bailey | |
| 2001/0036963 A1* | 11/2001 | Behrends et al. | 514/557 |
| 2004/0092588 A1 | 5/2004 | Kramer et al. | |
| 2005/0119313 A1* | 6/2005 | Behrends et al. | 514/334 |

FOREIGN PATENT DOCUMENTS

| | | | |
|---|---|---|---|
| DE | 39 25 540 | | 8/1990 |
| EP | 1 683 416 | | 7/2006 |
| WO | 02/069874 | | 9/2002 |
| WO | 03/067988 | | 8/2003 |
| WO | WO 2006099359 | * | 9/2006 |

OTHER PUBLICATIONS

English Language Abstract of DE 39 25 540, 1990.
Pitten, F.-A. et al., A standardized test to assess the impact of different organic challenges on the antimicrobial activity of antiseptics, Journal of Hospital Infection (2003), 55, 108-115.

* cited by examiner

*Primary Examiner* — Brian Gulledge
*Assistant Examiner* — Snigdha Maewall
(74) *Attorney, Agent, or Firm* — Nash and Titus, LLC

(57) ABSTRACT

Aqueous wound and mucous membrane disinfectant containing a) octenidine dihydrochloride, and b) one or more active ingredients selected from the group ethanol, 1-propanol, 2-propanol, undecylene amidopropyl trimonium methosulfate, 3-(4-chlorophenoxy)-1,2-propanediol and/or sodium hydroxymethylglycinate and c) glycerin and/or 1,2-diols having 3 to 10 carbon atoms, and d) optionally surfactants, emulsifiers, solubilizers, pH regulators, dyestuffs, perfumes and/or thickeners, the agent being free of phenoxyethanol, phenoxypropanol, phenoxyisopropanol and organic acids.

10 Claims, No Drawings

WOUND AND MUCOUS MEMBRANE DISINFECTANT

This application is it continuation application of U.S. Ser. No. 12/064,746, flied Jul. 31, 2006, now abandoned, which claims priority from international application PCT/EP2006/064836, filed Jul. 31, 2006, and further claims priority from German application 10 2005 041 730.2, filed Aug. 26, 2005 and German application 10 2005 058 978.2, filed Dec. 9, 2005.

BACKGROUND OF THE INVENTION

1. Field of the Invention

The present invention relates to an aqueous wound and mucous membrane disinfectant on the basis of octenidine dihydrochloride, which contains further ingredients from the group ethanol, propan-1-ol, propan-2-ol, undecylene amidopropyl trimonium methosulfate, sodium hydroxymethylglycinate, and 3-(4-chlorophenoxy)-1,2 propanediol. The disinfectant according to the present invention has a pH value of from 5 to 7 and is free of phenoxyethanol, phenoxypropanol, phenoxyisopropanol and organic acids.

2. Discussion of the Background Information

A wound and mucous membrane disinfectant should primarily meet certain microbiological requirements, which are described, for example, in F.-A. Pitten, H.-P. Werner, A. Kramer, "A standardized test to assess the impact of different organic challenges on the antimicrobial activity to antiseptics," Journal of Hospital Infection (2003) 55, 108-115. However, increasing importance is also being attached to the wound, skin or mucous membrane tolerance of a corresponding disinfectant.

Most of the active ingredients hitherto customary exhibit substantial deficits in terms of their tolerance. Iodine and PVP-iodine frequently trigger allergies with hypersensitivity, moreover, the skin is strongly colored and iodine, particularly from alcoholic solutions, penetrates through the skin and even more markedly through the mucous membrane, which can lead to hyperthyroidosis and even iodism in sensitive persons. Although these side effects are slighter with PVP-iodine, they are likewise manifest.

In addition to iodine and PVP-iodine and the alcohols, chlorhexidine and salts thereof are the most important active ingredients in antiseptics worldwide, although these compounds are viewed critically from a toxicological standpoint. Chlorhexidine is positive in the Ames Test and in the DNA Repair Test. Both results indicate a mutagenic potential. The breakdown products 4-chloraniline and 4-chlorophenyl isocyanate have a great affinity to the skin and concentrate there with frequent use. Triclosan, a chlorinated phenol, penetrates through the skin to a great extent and is a potential dioxin former.

Octenidine dihydrochloride is known as an active ingredient in mucous membrane and wound antiseptics and can be described by the limiting structure formulae below:

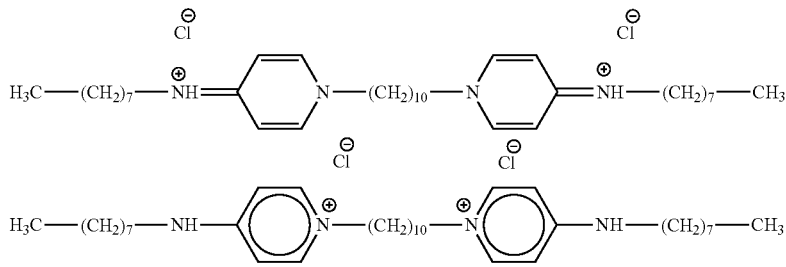

The raw material octenidine dihydrochloride has a good microbicidal effectiveness with relatively good tolerance. In DE 39 25 540 C1, an aqueous mucous membrane antiseptic is described, which contains phenoxyethanol and/or phenoxypropanol in addition to octenidine dihydrochloride to increase effectiveness. A preparation of this type is commercially available, e.g., under the name "Octenisept" and is often used in gynecology and andrology. However, recent tests have shown that the combination of octenidine dihydrochloride and phenoxyethanol has a high cytotoxicity, so that considerable reservations are justified regarding use on open wounds.

In WO-02/069874-A1 corresponding to DE 101 09 925-A1, wound and mucous membrane disinfectants are therefore described which, in addition to octenidine dihydrochloride, now contain ethanol and a physiologically tolerated organic acid instead of the above-referenced combination. The following are cited by way of example as organic acids: lactic acid, glycolic acid, malonic acid, succinic acid, malic acid, tartaric acid, or citric acid. The pH value of these solutions is 2.5 to 3.0. Acid preparations in this very low range can definitely be tolerated with infrequent use, but represent a noxa with longer-term application.

Basically all microbicidal active ingredients have a certain irritative potential, to which the mucous membranes react with particular sensitivity.

The object of the invention was therefore to develop a wound and mucous membrane disinfectant based on octenidine dihydrochloride, which on the one hand meets the microbicidal requirements—particularly with respect to the effectiveness regarding *Candida albicans*—but on the other hand has a more favorable pH value compared with the formulas of the prior art and thus a better wound, skin or mucous membrane tolerance.

Completely surprisingly and unforeseeable by one skilled in the art, these objects—particularly regarding the effectiveness with respect to *Candida albicans*—are met by an aqueous wound and mucous membrane disinfectant containing
  a) octenidine dihydrochloride,
  b) one or more active ingredients selected from the group ethanol, 1-propanol, 2-propanol, undecylene amidopropyl trimonium methosulfate, 3-(4-chlorophenoxy)-1,2-propanediol and/or sodium hydroxymethylglycinate,
  c) glycerin and/or 1,2-diols having from 3 to 10 carbon atoms, and d) optionally surfactants, emulsifiers, solubilisers, pH regulators, dyestuffs, perfumes and/or thickeners.

the agent being free of phenoxyethanol, phenoxypropanol, phenoxyisopropanol and organic acids.

SUMMARY OF THE INVENTION

Accordingly, the present invention provides an aqueous wound and mucous membrane disinfectant. The disinfectant comprises
(a) octenidine dihydrochloride;
(b) one or more active ingredients selected from ethanol, 1-propanol, 2-propanol, undecylene amidopropyl trimonium methosulfate, 3-(4-chlorophenoxy)-1,2-propanediol and/or sodium hydroxymethylglycinate; and
(c) at least one of glyderin and a 1,2-diol having from 3 to 10 carbon atoms, and is free of phenoxyethanol, phenoxypropanol, phenoxyisopropanol and organic acids.

In one aspect, the disinfectant may have a pH value of from 5 to 7.

In another aspect, component (b) of the disinfectant may comprise one or more of ethanol and 1-propanol and/or component (c) may comprise at least one of glycerin, 1,2-propanediol, 1,2-butanediol, 1,2-pentanediol and 1,2-hexanediol.

In another aspect, the disinfectant may comprise
(a) from 0.05% to 0.2% by weight of octenidine dihydrochloride;
(b) one or more of
 (i) from 0.5% to 15.0% by weight of one or more of 1-propanol, 2-propanol and ethanol
 (ii) from 0.5% to 5.0% by weight of undecylene amidopropyl trimonium methosulfate
 (iii) from 0.05% to 0.5% by weight of sodium hydroxymethylglycinate and
 (iv) from 0.03% to 0.3% by weight of 3-(4-chlorophenoxy)-1,2-propanediol; and
(c) from 0.2 to 3.0% by weight of at least one of glycerin and a 1,2-diol.

In yet another aspect, the disinfectant may consist of
(a) from 0.05% to 0.15% by weight of octenidine dihydrochloride;
(b) from 3.0% to 12.0% by weight of ethanol;
(c) from 0.3% to 1.0% by weight of glycerin (85% by weight); and
(d) water to 100% by weight;
or the disinfectant may consist of
(a) from 0.05% to 0.15% by weight of octenidine dihydrochloride;
(b) from 2.0% to 6.0% by weight of 1-propanol;
(c) from 0.3% to 1.0% by weight of glycerin (85% by weight); and
(d) water to 100% by weight.

In yet another aspect, the disinfectant of the Present invention may further comprise one or more additives selected from surfactants, emulsifiers, solubilizers, dyestuffs, pH regulators and/or thickeners. For example, the disinfectant may comprise one or more of ethoxylated glyceryl palmitate, ethoxylated sorbitan laurate, ethoxylated glyceryl isostearate, ethoxylated lauryl alcohol and cocamidopropyl betaine.

In a still further aspect, the disinfectant may further comprise from about 0% to 1.0% by weight of one or more surfactants and/or from about 0% to 5.0% by weight of one or more emulsifiers and/or may further comprise one or more thickeners selected from polyacrylic, natural and modified natural thickeners.

In another aspect, the pH of the disinfectant may have been adjusted by aqueous sodium hydroxide or phosphoric acid.

In yet another aspect, the disinfectant may be present as one or more of a liquid, a gel, a cream, a lotion, a spray and impregnated on a wipe or bandage.

The present invention also provides an aqueous wound and mucous membrane disinfectant, which disinfectant comprises
(a) octenidine dihydrochloride;
(b) one or more of ethanol and 1-propanol; and
(c) at least one of glycerin, 1,2-propanediol, 1,2-butanediol, 1,2-pentanediol and 1,2-hexanediol,
and is free of phenoxyethanol, phenoxypropanol, phenoxyisopropanol and organic acids and has a pH of from 5 to 7.

In one aspect, the disinfectant may further comprise one or more of ethoxylated glyceryl palmitate, ethoxylated sorbitan laurate, ethoxylated glyceryl isostearate, ethoxylated lauryl alcohol and cocamidopropyl betaine.

In another aspect, the disinfectant may further comprise from about 0% to 1.0% by weight of one or more surfactants and/or from about 0% to 5.0% by weight of one or more emulsifiers and/or may further comprise one or more thickeners selected from polyacrylic, natural and modified natural thickeners.

In yet another aspect, the pH of the disinfectant may have been adjusted by aqueous sodium hydroxide or phosphoric acid.

DETAILED DESCRIPTION OF THE INVENTION

Particularly preferred components according to the invention according to b) are 1-propanol and ethanol. Particularly preferred ingredients according to the invention according to c) are glycerin, 1,2-propanediol, 1,2-butanediol, 1,2-pentanediol and/or 1,2-hexanediol.

It is advantageous for the purposes of the present invention to select the content of octenidine dihydrochloride from the range of 0.05 to 0.2% by weight. Particularly preferably, the content of octenidine dihydrochloride is approx. 0.1% by weight, in order to achieve a very good microbicidal effectiveness with at the same time excellent skin tolerance.

It is preferred for the purposes of the present invention if the wound and mucous membrane disinfectant according to the invention contains
a) 0.05 to 0.2% by weight of octenidine dihydrochloride and
b) respectively 0.5 to 15.0% by weight of 1-propanol and/or 2-propanol and/or ethanol and/or 0.5 to 5.0% by weight of undecylene amidopropyl trimonium methosulfate and/or 0.05 to 0.5% by weight of sodium hydroxymethylglycinate and/or 0.03 to 0.3% by weight of 3-(4-chlorophenoxy)-1,2-propanediol and
c) 0.2 to 3.0% by weight of glycerin and/or 1,2-diols.

A wound and mucous membrane disinfectant according to the invention is particularly preferred which consists of:
a) 0.05 to 0.15% by weight of octenidine dihydrochloride
b) 3.0 to 12.0% by weight of ethanol
c) 0.3 to 1.0% by weight of glycerin (85% by weight),
d) water to 100% by weight.

Furthermore, a wound and mucous membrane disinfectant is particularly preferred according to the invention having
a) 0.05 to 0.15% by weight of octenidine dihydrochloride,
b) 2.0 to 6.0% by weight of 1-propanol,
c) 0.3 to 1.0% by weight of glycerin (85% by weight)
d) water to 100% by weight.

The wound and mucous membrane disinfectants according to the invention can in addition contain other substances such as dyestuffs, perfumes, emulsifiers, solubilizers, pH regulators, thickeners and/or surfactants. Preferably according to the invention, only those substances are taken into consideration for this purpose that have no or only a very low additional irritative potential.

This requirement naturally applies particularly to the surfactants and emulsifiers. Surfactants and emulsifiers are accordingly particularly suitable for an application for the purposes of the present invention which show no or only a very low irritative potential in the red blood cell test (RBC test) code 11035 and/or in the hen's egg test chorioallantoic membrane code 11087 (HET-CAM test). With regard to a more exact gradation between the surfactants and emulsifiers, reference is thereby made, inter alia, to the relevant literature on the above topic.

Particularly advantageously according to the invention only small amounts—if any—of surfactants and emulsifiers which are very well tolerated by mucous membranes should e.g., per se (i.e., in the form of an aqueous solution), as a gel or as an impregnation solution for wipes and/or bandages. However, the wound or mucous membrane disinfectant for the purpose of the present invention can furthermore preferably also represent the aqueous phase of an emulsion that furthermore contains as oil phase those lipids that are known to be particularly well tolerated by wounds and mucous membranes, such as, e.g., natural oils or modified oils and fats (e.g., almond oil, hydrogenated castor oil).

The subject of the present invention are therefore also O/W or W/O emulsions—e.g., in the form of a cream, lotion or a spray—which comprise the aqueous mucous membrane disinfectant.

The present invention is described in more detail by the following examples, but without being limited thereby.

EXAMPLES

| Raw materials | 1 | 2 | 3 | 4 | 5 | 6 | 7 | 8 | 9 | 10 | 11 | 12 |
|---|---|---|---|---|---|---|---|---|---|---|---|---|
| Octenidine dihydrochloride | 0.1 | 0.1 | 0.1 | 0.05 | 0.15 | 0.1 | 0.1 | 0.1 | 0.05 | 0.2 | 0.1 | 0.1 |
| Ethanol (99% by weight) | 10.0 | | | 12.0 | 3.0 | 7.0 | 7.0 | | | | | 15.0 |
| 1-Propanol | | 4.0 | | | | | 3.0 | | 15.0 | | | |
| 2-Propanol | | | 4.0 | | 2.0 | | | | | 1.0 | | |
| Undecylene amidopropyl trimonium methosulfate | | | | 2.1 | | | | | 4.1 | 1.1 | | |
| Sodium hydroxymethylglycinate | | | | | | 0.05 | | | 0.5 | | | |
| 3-(4-Chlorophenoxy)-1,2-propanediol | | | | | | | | | | 0.03 | | 0.3 |
| Glycerin (85% by weight) | 0.5 | 0.5 | 0.5 | 1.5 | | 3.0 | 1.5 | 0.5 | 0.5 | | 0.5 | |
| 1,2-Pentanediol | | | | | 1.0 | | | | 0.5 | 0.2 | | 3.0 |
| NaOH solution | Var. | Var. | Var. | Var. | Var. | Var. | Var. | Var. | Var. | Var. | Var. | Var. |
| Phosphoric acid solution | Var. | Var. | Var. | Var. | Var. | Var. | Var. | Var. | Var. | Var. | Var. | Var. |
| Water | ad 100 | ad 100 | ad 100 | ad 100 | ad 100 | ad 100 | ad 100 | ad 100 | ad 100 | ad 100 | ad 100 | ad 100 |

Quantities in % by weight be used, since otherwise, inter alia, an excessive irritation of the mucous membranes may occur.

Surfactants that are suitable and accordingly advantageously to be used for the purpose of the present invention are, for example, ethoxylated glyceryl palmitate (INCI name: PEG-200 hydrogenated glyceryl palmate), ethoxylated sorbitan laurate (INCI: PEG-80 sorbitan laurate), ethoxylated glyceryl isostearate (INCI: PEG-90 glyceryl isostearate), ethoxylated lauryl alcohol (INCI: laureth-2) or also betaines such as, e.g., cocamidopropyl betaine (INCI), a concentration between 0 and 1.0% by weight having proven advantageous. With regard to the emulsifiers, reference is made by way of example to the ethoxylated fatty alcohols or also fatty acid esters (INCI: ceteareth-20, glyderyl stearate).

The wound and mucous membrane disinfectants according to the invention are clear solutions with a pH value of from 5 to 7. This pH value results, for example, in the particularly preferred formula "by itself," as it were. In other cases it may be necessary to adjust the pH value accordingly. According to the invention, aqueous sodium hydroxide or phosphoric acid have proven useful for this purpose.

The wound and mucous membrane disinfectants can advantageously also contain thickeners for the purpose of the present invention. Synthetic polymers on a polyacrylic acid basis or natural thickeners, such xanthan gum or modified natural types of thickeners, such as, e.g., cellulose derivatives, are preferably to be used according to the invention.

The wound and mucous membrane disinfectant according to the invention can be used in different application forms, Tolerance tests were carried out on scarified skin. It was shown thereby that the wound and mucous membrane disinfectants according to the invention are better tolerated than the preparations of the prior art.

What is claimed is:

1. A method to disinfect an open wound or mucous membrane while minimizing irritation to the wound or membrane site, comprising the steps of
   A. applying to the site of an open wound or mucous membrane a microbiocidally effective amount of an aqueous composition comprising
      (a) from 0.05% to 0.2% by weight of octenidine dihydrochloride;
      (b) one or more of
         (i) from 0.5% to 15.0% by weight of one or more of 1-propanol, 2-propanol and ethanol
         (ii) from 0.5% to 5.0% by weight of undecylene amidopropyl trimoniun methosulfate
         (iii) from 0.05% to 0.5% by weight of sodium hydroxymethylglycinate and
         (iv) from 0.03% to 0.3% by weight of 3-(4-chlorophenoxy)-1,2-propanediol;
      (c) from 0.2 to 3.0% by weight of at least one of glycerin and a 1,2-diol, and
      (d) optionally, aqueous sodium hydroxide or phosphoric acid,
   wherein the composition is free of phenoxyethanol, phenoxypropanol, phenoxyisopropanol and organic acids, and has a pH value of from 5 to 7; and B. allowing the composition to remain on the site until the site is disinfected, wherein the site tolerates the composition with minimal irritation.

2. The method of claim 1, wherein (b) is one or both of ethanol and 1-propanol.

3. The method of claim 1, wherein (c) is at least one of glycerin, 1,2-propanediol, 1,2-butanediol, 1,2-pentanediol and 1,2-hexanediol.

4. The method of claim 1, wherein the disinfectant consists essentially of
   (a) from 0.05% to 0.2% by weight of octenidine dihydrochloride;
   (b) one or more of
      (i) from 0.5% to 15.0% by weight of one or more of 1-propanol, 2-propanol and ethanol
      (ii) from 0.5% to 5.0% by weight of undecylene amidopropyl trimoniun methosulfate
      (iii) from 0.05% to 0.5% by weight of sodium hydroxymethylglycinate and
      (iv) from 0.03% to 0.3% by weight of 3-(4-chlorophenoxy)-1,2-propanediol;
   and
   (c) from 0.2 to 3.0% by weight of at least one of glycerin and a 1,2-diol, and
   (d) optionally, aqueous sodium hydroxide or phosphoric acid,
   the disinfectant being free of phenoxyethanol, phenoxypropanol, phenoxyisopropanol and organic acids,
   wherein the disinfectant has a pH value of from 5 to 7.

5. The method of claim 1, wherein the disinfectant comprises
   (a) from 0.05% to 0.15% by weight of octenidine dihydrochloride;
   (b) from 3.0% to 12.0% by weight of ethanol;
   (c) from 0.3% to 1.0% by weight of glycerin (85% by weight); and
   (d) water to 100% by weight.

6. The method of claim 1, wherein the disinfectant comprises
   (a) from 0.05% to 0.15% by weight of octenidine dihydrochloride;
   (b) from 2.0% to 6.0% by weight of 1-propanol;
   (c) from 0.3% to 1.0% by weight of glycerin (85% by weight); and
   (d) water to 100% by weight.)

7. The method of claim 1, wherein the disinfectant is applied as a liquid.

8. The method of claim 1, wherein the disinfectant is applied to an open wound or mucous membrane as an aqueous solution, as a gel, as an impregnation solution for wipes and/or bandages, or as an aqueous phase of an emulsion.

9. The method of claim 8, wherein the emulsion contains an oil phase comprising natural oils, modified oils and/or fats.

10. The method of claim 1, wherein the disinfectant is applied in a cream, lotion or a spray.

* * * * *